(12) United States Patent
Takeuchi et al.

(10) Patent No.: US 7,234,458 B2
(45) Date of Patent: *Jun. 26, 2007

(54) LAMINATED HEATING BODY

(75) Inventors: Naohito Takeuchi, Kagawa (JP); Toshiyuki Tanio, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 24 days.

This patent is subject to a terminal disclaimer.

(21) Appl. No.: 10/348,294

(22) Filed: Jan. 21, 2003

(65) Prior Publication Data

US 2003/0141293 A1    Jul. 31, 2003

(30) Foreign Application Priority Data

Jan. 31, 2002    (JP)    .............................. 2002-023267

(51) Int. Cl.
F24J 1/00    (2006.01)
A61F 7/00    (2006.01)

(52) U.S. Cl. ................. 126/263.02; 126/204; 607/114; 604/291

(58) Field of Classification Search ........... 126/263.05, 126/263.12, 263.07, 204, 206, 263.02; 607/96, 607/114, 109–113, 289, 108; 62/4; 428/702; 604/289, 291

See application file for complete search history.

(56) References Cited

U.S. PATENT DOCUMENTS

| | | | | |
|---|---|---|---|---|
| 3,643,665 A | | 2/1972 | Caillouette | |
| 3,736,769 A | * | 6/1973 | Petersen | 62/530 |
| 4,925,743 A | * | 5/1990 | Ikeda et al. | 428/702 |
| 5,046,479 A | * | 9/1991 | Usui | 126/204 |
| 5,366,492 A | * | 11/1994 | Ueki | 126/263.07 |
| 5,662,624 A | * | 9/1997 | Sundstrom et al. | 604/291 |
| 5,879,378 A | * | 3/1999 | Usui | 607/96 |
| 6,183,855 B1 | | 2/2001 | Buckley | |
| 6,465,709 B1 | * | 10/2002 | Sun et al. | 602/48 |
| 6,893,453 B2 | * | 5/2005 | Agarwal et al. | 607/108 |

FOREIGN PATENT DOCUMENTS

| | | |
|---|---|---|
| EP | 1 147 752 A1 * | 10/2001 |
| EP | 1181911 A1 | 2/2002 |
| JP | 64-034363 | 2/1989 |
| JP | 10-108875 * | 4/1998 |
| JP | 2001031559 A1 | 2/2001 |
| JP | 2001-161737 * | 6/2001 |
| WO | WO-94/16653 A1 | 8/1994 |

OTHER PUBLICATIONS

Computer translation of JP 10-108875 which was previously cited in Office action mailed Jun. 7, 2004.*

* cited by examiner

Primary Examiner—Josiah C. Cocks
(74) Attorney, Agent, or Firm—Darby & Darby

(57) ABSTRACT

A laminated heating body permits free adjustment of temperature to be felt on a user's skin by varying condition of a cover sheet on a surface thereof. The laminated heating body includes a heating body and a cover sheet covering the heating body. The cover sheet is formed from a laminated sheet consisted of at least two sheet bases having mutually different heat conductivity. At least two sheet bases are peelably bonded with each other.

9 Claims, 2 Drawing Sheets

LAMINATED HEATING BODY

CROSS REFERENCE TO THE RELATED APPLICATION

The present application has been filed with claiming priority based on Japanese Patent Application No. 2002-23267, filed on Jan. 31, 2002. Disclosure of the above-identified Japanese Patent Application is herein incorporated by reference.

BACKGROUND OF THE INVENTION

1. Field of the Invention

The present invention relates generally to a laminated heating body to be used as heating body for a disposable warmer and so forth, for example. More particularly, the invention relates to a laminated heating body which can arbitrarily set a temperature on a surface of a sheet.

2. Description of the Related Art

A warmer, such as disposable warmer, is a laminate body of a heating body and a cover sheet wrapping the heating body. The cover sheet is typically formed into a bag shape for achieving a function for sealingly enclosing the heating body received therein and a function for transmitting heat generated from the heating body to a user skin. In case of the conventional disposable warmer, the cover sheet is formed from non-woven fabric or the like.

On the other hand, in Japanese Unexamined Patent Publication No. Showa 64(1989)-034363, an invention relating to a heating device featured in a surface member covering a heating body is disclosed.

The heating device disclosed in the above-identified publication has a surface film covering the heating body, in which the surface film has gas permeability. A plurality of adhesive tapes having a function for blocking gas permeability of the surface film, are fitted on the surface of the surface film. By peeling off the adhesive tapes, an exposure area of the surface film having gas permeability can be varied to adjust a supply amount of air contributing for oxidation reaction of the heating body and whereby to control temperature profile.

However, in case of the disposable warmer, in which the heating body is covered by a non-woven fabric as in the prior art, efficiency in transferring a heat generated by the heating body to a skin of a user, can be low.

On the other hand, in case of the heating device disclosed in the above-identified publication, gas permeable area of the surface film is adjusted by peeling off the adhesive tapes to adjust the supply amount of air contributing for oxidation reaction of the heating body, as set forth above. However, it is actually difficult to control heating amount of the heating body by controlling oxidation reaction of the heating body. Therefore, heating amount can be lacking or excessive to cause difficulty in setting an optimal temperature.

SUMMARY OF THE INVENTION

Therefore, the present invention has been worked out in view of the shortcoming encountered in the prior art. It is an object of the present invention to provide a laminated heating body which permits free adjustment of temperature to be felt on a user's skin by varying condition of a cover sheet on a surface thereof.

According to one aspect of the invention, a laminated heating body comprises:

a heating body; and a cover sheet covering the heating body, the cover sheet being formed from a laminated sheet consisted of at least two sheet bases having mutually different heat conductivity, the at least two sheet bases being peelably bonded with each other.

In the laminated heating body set forth above, by exposing the sheet bases having different heat conductivities on the surface of the cover sheet, temperature to be sensed on the user's skin can be varied for adjusting the surface temperature of the laminated heating body depending upon condition, such as environmental temperature.

The cover sheet may be consisted of one sheet base located in contact with the heating body and having higher heat conductivity than that of the other sheet base laminated on a surface of the one sheet base remote from the heating body.

With the construction set forth above, by peeling off the sheet base, the surface temperature of the laminated heating body can be made gradually higher to permit selection of the surface temperature.

The sheet base having the greatest heat conductivity may be moisture impermeable.

In this case, the heating body may cause oxidation reaction by oxygen introduced through the back sheet to cause heat generation.

BRIEF DESCRIPTION OF THE DRAWINGS

The present invention will be understood more fully from the detailed description given hereinafter and from the accompanying drawings of the preferred embodiment of the present invention, which, however, should not be taken to be limitative to the invention, but are for explanation and understanding only.

In the drawings.

DESCRIPTION OF THE PREFERRED EMBODIMENT

The present invention will be discussed hereinafter in detail in terms of the preferred embodiment of the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structure is not shown in detail in order to avoid unnecessary obscurity of the present invention.

Figure 1:
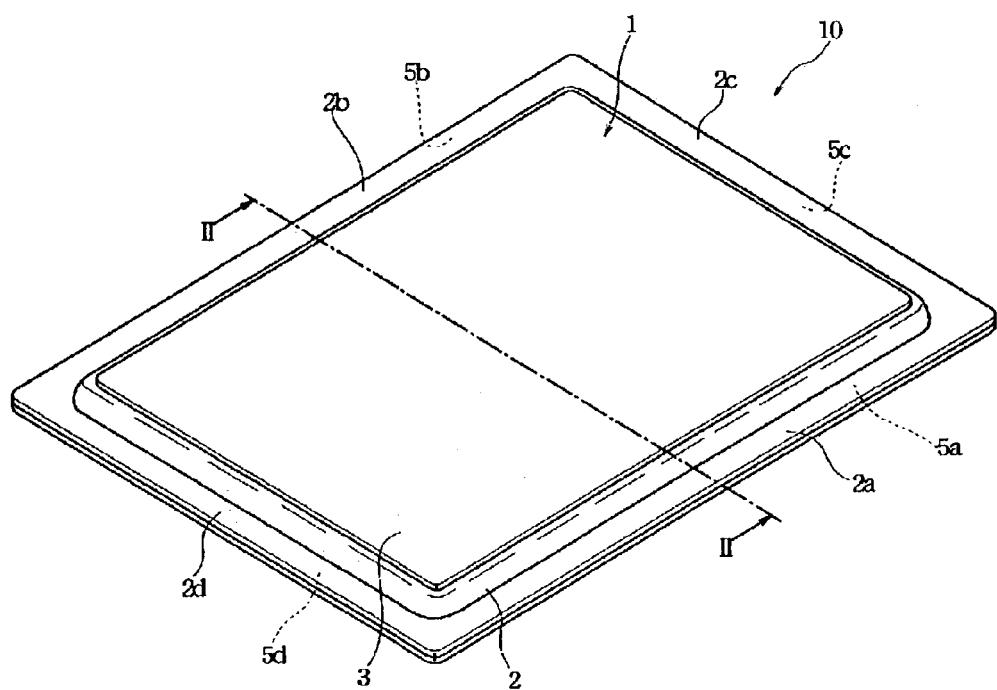
FIG. 1 is a perspective view of the preferred embodiment of a laminated heating body according to the present invention.
Figure 2:
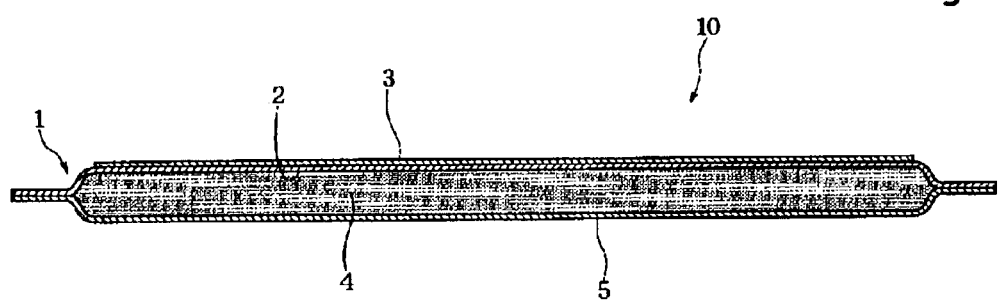
FIG. 2 is a section of the laminated heating body taken along line II—II of FIG. 1.
Figure 3:
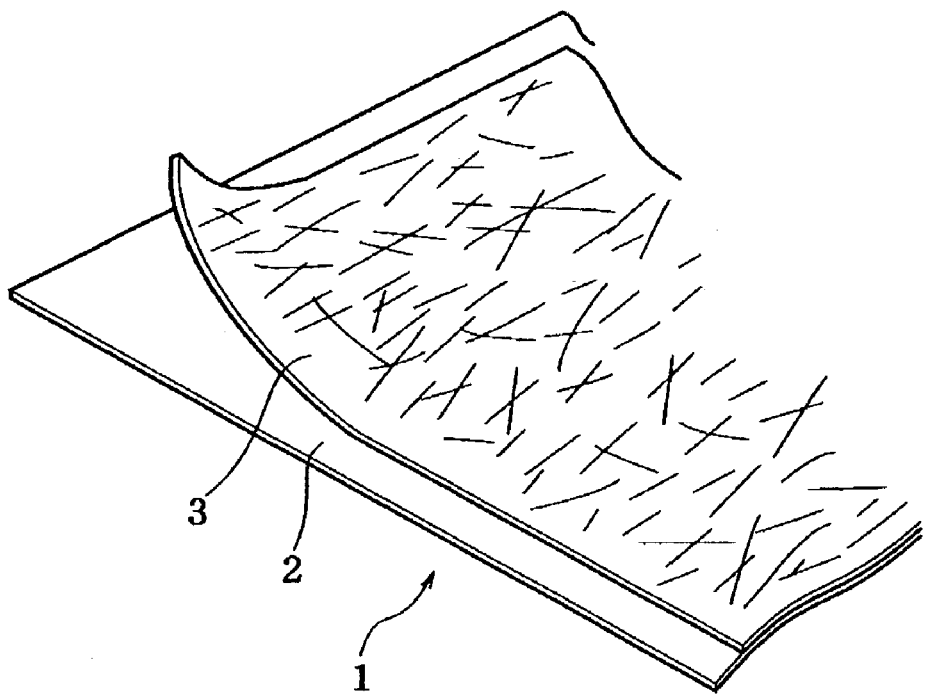
FIG. 3 is a partial perspective view showing a structure of a cover sheet.

FIG. 1 is a perspective view of the preferred embodiment of a laminated heating body according to the present invention, FIG. 2 is a section of the laminated heating body taken along line II—II of FIG. 1, and FIG. 3 is a partial perspective view showing a structure of a cover sheet.

A laminated heating body 10 shown in FIGS. 1 and 2 is applicable for a disposable warmer or the like. The shown embodiment of the laminated heating body includes a heating body 4, a cover sheet 1 covering a front side surface of the heating body 4, and a back sheet 5 covering a back side surface of the heating body 4.

The heating body 4 is formed by mixing metal powder, such as iron powder or the like, reaction auxiliary agent, such as sodium chloride or the like, activated charcoal, water, moisture holding agent and so forth.

The cover sheet 1 is formed by laminating a second sheet base 3 on a first sheet base 2. The second sheet base 3 is detachably laminated on the surface of the first sheet base 2. As shown in FIGS. 1 and 2, the first sheet base 2 is formed into a size equal to the laminated heating body 10. The second sheet base 3 is formed into a size slightly smaller than the first sheet base 2. By forming the second sheet base 3 slightly smaller than the first sheet base 2, the edge portion of the second sheet base 3 can be easily gripped for peeling off the surface of the first sheet base 2.

However, a relationship of the sizes of the first sheet base 2 and the second sheet base 3 in the cover sheet 1 is not limited to that set forth above. The first and second sheet bases 2 and 3 may be the same size. In the alternative, the second sheet base 3 may be greater than the first sheet base 2.

In the condition where the heating body 4 is disposed between the first sheet base 2 of the cover sheet 1 and the back sheet 5, a right side edge 2a of the first sheet base 2 and a right side edge 5a of the back sheet 5, a left side edge 2b of the first sheet base 2 and a left side edge 5b of the back sheet 5, a front edge 2c of the first sheet base 2 and a front edge 5c of the back sheet 5, and a rear edge 2d of the first sheet base 2 and a rear edge 5d of the back sheet 5 are bonded by hot melt adhesive, heat seal and so forth, respectively.

In the cover sheet 1, the first sheet base 2 and the second sheet base 3 are sheets having mutually different heat conductivity. Preferably, the first sheet base 2 has greater heat conductivity than that of the second sheet base 3.

Throughout the disclosure, "heat conductivity" means a ratio of a heat flow flowing through a unit area in an isothermal surface within a substance in a direction perpendicular thereto in a unit period and a temperature gradient in the flow direction of the heat flow. Accordingly, when heat is applied to the cover sheet 1 from the heating body 4, a temperature on the surface of the first sheet base 2 becomes higher than a temperature on the surface of the second sheet base 3.

When the surface temperature of the first sheet base 2 and the surface temperature of the second sheet base 3 are measured while the heating body 4 is heated, it is preferred that a temperature difference between the surface of the first sheet base 2 and the second sheet base 3 after 60 minutes from starting heating of the heating body 4 is preferably in a range of 1 to 4° C. Such temperature difference between the first sheet base 2 and the second sheet base 3 provides temperature gradient on the surface of the cover sheet contacting with the user's skin. When the temperature difference between the first sheet base 2 and the second sheet base 3 is greater than or equal to 1° C., temperature gradient on the surface of the cover sheet becomes sufficient to prevent dulling of temperature sensitivity of the skin when the second sheet base 3 is peeled off to directly contact the surface of the first sheet base 2 on the user's skin, so that apparent temperature difference can be perceived. On the other hand, if the temperature difference is smaller than 1° C., the user's skin may be easily dulled to loose warm feeling since directly contacting the first sheet base 2 onto the user's skin with peeling the second sheet base 3 off the surface of the first sheet base 2. If the temperature difference is greater than 4° C., user's skin may be irritated for excessively high temperature.

The first sheet base 2 having greater heat conductivity may be a composite sheet formed by laminating a metal foil and a plastic film, a sheet formed by depositing a metal film on the plastic film, or a sheet formed from the plastic film containing metal powder having high heat conductivity, for example. In this case, plastic material forming the plastic film may be polypropylene, polyester or the like.

On the other hand, the metal may be a metal foil or one which can be deposited. As suitable metal, gold, silver, copper, chrome, aluminum or the like may be used. On the other hand, as suitable powder or particle state metal material to be mixed in the plastic, magnesium, molybdenum, zinc, tungsten, cadmium, nickel, rhodium, iron or the like may be used.

On the other hand, the second sheet base 3 having smaller heat conductivity may be polyethylene film, polypropylene film, nylon film, polyester film, spun-bonded non-woven fabric fabricated by polypropylene fibers, laminated sheet formed by laminating spun-bonded non-woven fabric/melt-blown non-woven fabric/spun-bonded non-woven fabric in sequential order, spun-laced non-woven fabric fabricated by applying high pressure water jet to a fiber web formed from polyester fibers, polypropylene fibers and rayon fibers for entangling fibers, a sheet integrally formed with laminating a spun-bonded non-woven fabric formed from nylon fibers and polyethylene film, and other suitable sheet material.

Preferably, both of the first sheet base 2 and the second sheet base 3 are gas permeable sheets. When resin film is used as the first and/or second sheet bases 2 and 3, the resin films to be used are porous films or are gas impermeable films formed with pores. By forming the first and second sheet bases 2 and 3 with providing gas permeability, air is supplied to the heating body 4 for causing oxidation reaction therein and whereby for promoting heating.

On the other hand, means for peelably bonding the second sheet base 3 on the surface of the first sheet base 2 is required to permit easy peeling of the sheet bases and not to degrade gas permeability of the cover sheet 1. For example, a plurality of dot form hot melt adhesives bonding the first and second sheet bases 2 and 3 at several positions and a plurality of dot form heat seal portions fuse-bonding the first and second sheet bases 2 and 3 at several positions may be employed as means for peelably bonding the sheet bases.

In the alternative, it is also possible to apply a pressure sensitive adhesive on the back surface along the periphery of the second sheet base 3 located at the surface side of the first sheet base 2.

Next, the back sheet 5 is formed from a resin sheet. It should be noted that the back sheet 5 has gas permeability so as to promote oxidation reaction of the internal heating body 4 for heating. For example, the back sheet 5 may be produced by melt extrusion of polypropylene resin or polyethylene resin blended inorganic filler into a film to form pore in the portion of the inorganic filler. In the alternative, the back sheet 5 may be formed by the same non-woven fabric as the first sheet base 2. In the further alternative, the back sheet 5 may be formed by a combination of the first sheet base 2 and the second sheet base 3 similarly to the cover sheet 1.

The laminated heating body 10 is sealingly enclosed in a gas impermeable film package before use. By opening the film package, air is supplied to the heating body 4 through the first sheet base 2 and/or the back sheet 5 to cause oxidation reaction in the heating body 4 for heating.

Heat generated by the heating body 4 is transferred to the user's skin through the cover sheet 1. In the initial state, since the second sheet base 3 having relatively small heat conductivity is appearing on the surface of the first sheet base 2, the temperature on the surface of the cover sheet 1 can be held relatively low.

When the second sheet base 3 is peeled off, the first sheet base 2 having relatively greater heat conductivity appears on the surface of the cover sheet 1 to transfer greater amount of heat to the user's skin to cause high temperature feeling.

With the construction set forth above, the user may adjust heat to be transferred to the user's skin by selecting either the second sheet base 3 is peeled off the surface of the first sheet base 2 or the second sheet base 3 is maintained on the surface of the first sheet base 2 depending upon environmental temperature, amount of wearing cloths, and presence or absence of heater.

Figure 4:
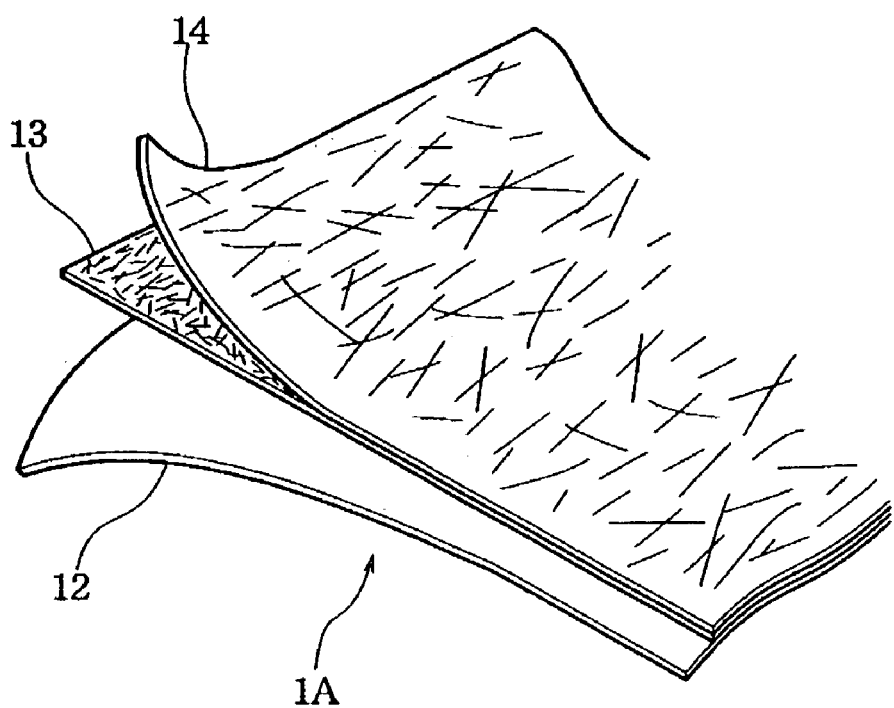
FIG. 4 is a partial perspective view showing another embodiment of the cover sheet.

Next, FIG. 4 is a partial perspective view showing another embodiment of the cover sheet of the laminated heating body.

A cover sheet 1A covers the surface of the heating body 4 of the laminated heating body shown in FIGS. 1 and 2, and is formed by laminating a first sheet base 12, a second sheet base 13 and a third sheet base 14 in sequential order from the heating body 4 side. The third sheet base 14 is peelably bonded on the surface of the second sheet base 13. The second sheet base 13 is peelably bonded on the surface of the first sheet base 12.

The first, second and third sheet bases 12, 13 and 14 are respectively formed from sheet materials having different heat conductivities. In the shown embodiment, the heat conductivity of the first sheet base 12 is greater than that of the second sheet base 13, and the heat conductivity of the second sheet base 13 is greater than that of the third sheet base 14.

For example, the first and second sheet bases 12 and 13 are formed from composite sheets of resin material and metal material. In the first and second sheet bases, kinds of metals are differentiated, or in the alternative, amount of metals to be contained in the composite sheets are differentiated so that the first sheet base 12 may have greater heat conductivity than the second sheet base 13. On the other hand, the third sheet base 14 may be formed from a resin film or non-woven fabric.

In the laminated heating body employing the cover sheet 1A, the surface temperature of the cover sheet 1A can be higher when the third sheet base 14 is peeled off the second sheet base 13 than that of the cover sheet 1A when the third sheet base 14 is placed on the surface of the cover sheet 1A as bonded on the surface of the second sheet base 13. By further peeling off the second sheet base 13 from the surface of the first sheet base 12, the surface temperature of the cover sheet 1A becomes further higher.

On the other hand, when the cover sheet is formed with two sheet bases as shown in FIG. 3, it is possible to provide greater heat conductivity for the second sheet base 3 located on outer side than that of the first sheet base 2 located on closer side of the heating body 4. Even in this case, temperature difference can be provided between the case when the second sheet base 3 on the surface side is maintained on the surface of the first sheet base 2 and the case when the first sheet base 2 is exposed by peeling off the second sheet base 3. Also, as modifications of the cover sheet 1A of FIG. 4, the heat conductivities can be set to sheet base 12<sheet base 13<sheet base 14, or sheet base 13<sheet base 12<sheet base 14.

EXAMPLE

The laminated heating body 10 having structure shown in FIG. 1 was formed.

As the first sheet base 2, a moisture impermeable composite film formed by laminating polyester film of 12 μm thick/aluminum foil of 6 μm thick/polypropylene film of 20 μm thick was used.

As the second sheet base 3, a laminated sheet of a spun-bonded non-woven fabric of nylon fibers to have basis weight of 18 g/m$^2$ and a polyethylene film of 20 μm thick was used.

The back sheet 5 was formed from a laminated sheet of a spun-bonded non-woven fabric of nylon fibers to have basis weight of 35 g/m$^2$ and a moisture permeable polyethylene film of 60 μm thick. The back sheet having total basis weight of 116 g/m$^2$ was used. A moisture permeability as measured according to JIS-K7129 (Testing methods for water vapor transmission rate of plastic film and sheeting (instrument method)) was 431 ml/m$^2$·day.

On the other hand, as the heating body 4, "Hokaron" (tradename) available from Lotte Denshi Kogyo Kabushiki Kaisha was used.

The surface temperature of the laminated heating body 10 was measured by a temperature measurement device (Thermo-recorder "RT-10": Tabai Espec Kabushiki Kaisha). A gauge head of the temperature measurement device was contacted on the surface of the first sheet base 2 and the surface of the second sheet base 3. Then, the laminated heating body 10 was wrapped with a four-fold towel and temperatures of the surfaces of the first sheet base 2 and the second sheet base 3 were measured at respective timings set out below. An environment of measurement was 25° C. in temperature and 65% in relative humidity.

At timings of 60 minutes after starting heating, the surface temperature of the first sheet base 2 was 51.2° C. and the surface temperature of the second sheet base 3 was 49.0° C. At timings of 300 minutes after starting heating, the surface temperature of the first sheet base 2 was 52.3° C. and the surface temperature of the second sheet base 3 was 49.2° C. At timings of 600 minutes after starting heating, the surface temperature of the first sheet base 2 was 48.6° C. and the surface temperature of the second sheet base 3 was 43.5° C.

As set forth above, the laminated heating body according to the present invention may adjust the surface temperature by peeling off the surface member adapting to the environmental temperature.

Although the present invention has been illustrated and described with respect to exemplary embodiment thereof, it should be understood by those skilled in the art that the foregoing and various other changes, omission and additions may be made therein and thereto, without departing from the spirit and scope of the present invention. Therefore, the present invention should not be understood as limited to the specific embodiment set out above but to include all possible embodiments which can be embodied within a scope encompassed and equivalent thereof with respect to the feature set out in the appended claims.

For instance, it is possible to locally provide temperature difference by partly peeling one sheet base from the other sheet base to provide high heat conductivity portions and low heat conductivity portions as disclosed or suggested in commonly assigned co-pending U.S. Patent Application, for "Laminated Heating Body", filed with claiming the convention priority based on Japanese Patent Application No. 2002-23263, filed on Jan. 31, 2002. The disclosure of the above-identified co-pending U.S. Patent Application is herein incorporated by reference.

What is claimed is:

1. A laminated heating body for transmitting heat to a user's skin, comprising:
    a heating body for generating heat; and
    a cover sheet covering a skin-facing side of said heating body, said cover sheet being a laminate of first, second and third sheet bases, said first sheet base being in contact with said heating body, said second sheet base being peelably bonded on a skin-facing side of said first sheet base remote from said heating body, said third sheet base being peelably bonded on a skin-facing side of said second sheet base remote from said heating body,
    wherein said first sheet base is moisture impermeable, the second and third sheet bases are peelably removable for adjusting the transfer of heat from the heating body to the user's skin, said first sheet base includes metal so as to have a higher heat conductivity than the second sheet base, and said third sheet base has a heat conductivity different from those of said first and second sheet bases.

2. A laminated heating body as set forth in claim 1, wherein said second sheet base has a higher heat conductivity than said third sheet.

3. A laminated heating body as set forth in claim 2, wherein said first and second sheet bases are both formed from resin and metal, but contains either different kinds or different amounts of metal to make the heat conductivity of the first sheet base higher than that of the second sheet base.

4. A laminated heating body as set forth in claim 3, wherein said third sheet base is formed from a non-woven fabric.

5. A laminated heating body as set forth in claim 1, wherein said first sheet base is a composite film formed by laminating a metal foil and a plastic film.

6. A laminated heating body as set forth in claim 1, wherein when a surface temperature of said first sheet base and a surface temperature of said second sheet base are measured while said heating body is generating heat, a temperature difference between said first sheet base and second sheet base after 60 minutes from start of heat generation of said heating body is in a range of 1 to 4° C.

7. A laminated heating body as set forth in claim 1, further comprising a back sheet covering a back side of said heating body, such that said heating body is disposed between said cover sheet and said back sheet.

8. A laminated heating body as set forth in claim 1, wherein the heating body contains a metal powder to generate heat by an oxidation reaction.

9. A laminated heating body as set forth in claim 8, wherein said metal powder is iron powder.

* * * * *